United States Patent [19]
Collins

[11] Patent Number: 4,505,710
[45] Date of Patent: Mar. 19, 1985

[54] IMPLANTABLE FLUID DISPENSING SYSTEM

[76] Inventor: Earl R. Collins, 801 Craig Ave., La Canada, Calif. 91011

[21] Appl. No.: 494,544

[22] Filed: May 13, 1983

[51] Int. Cl.³ ............................................. A61M 7/00
[52] U.S. Cl. .................................... 604/891; 604/131; 604/892
[58] Field of Search ...................... 604/66, 50, 31, 131, 604/140, 143, 144, 891, 892; 222/146 HE, 94, 214

[56] References Cited

U.S. PATENT DOCUMENTS

| | | | |
|---|---|---|---|
| 3,951,147 | 4/1976 | Tucker et al. | 604/891 X |
| 4,056,095 | 11/1977 | Rey et al. | 604/891 X |
| 4,112,947 | 9/1978 | Nehring | 604/131 X |
| 4,140,122 | 2/1979 | Kuhl et al. | 604/891 |
| 4,335,835 | 6/1982 | Beigler et al. | 604/131 X |
| 4,360,019 | 11/1982 | Portner et al. | 604/892 X |

Primary Examiner—Edward M. Coven
Attorney, Agent, or Firm—James T. English

[57] ABSTRACT

A drug dispensing device for in-vivo implantation has a diaphragm defining a movable wall of a container for drug fluid, the diaphragm being moved by expanding gas volumes differentially activated by electric heater means controlled by a calendar-clock to induce drug fluid through a constant flow valve in one wall of the container and into the living organism, discretely, or continuously over a period of time or at intervals controlled by the clock. The container is refilled with fresh drug by injection through the skin and a puncturable seal valve while the diaphragm is actuated in a reverse direction by heater activation. The dispensing program can be changed externally by electromagnetically coupled signals; the controller batteries can be similarly recharged by external coupling to a power source. Freshness of the drug and the size of the container determine the time between refills.

5 Claims, 6 Drawing Figures

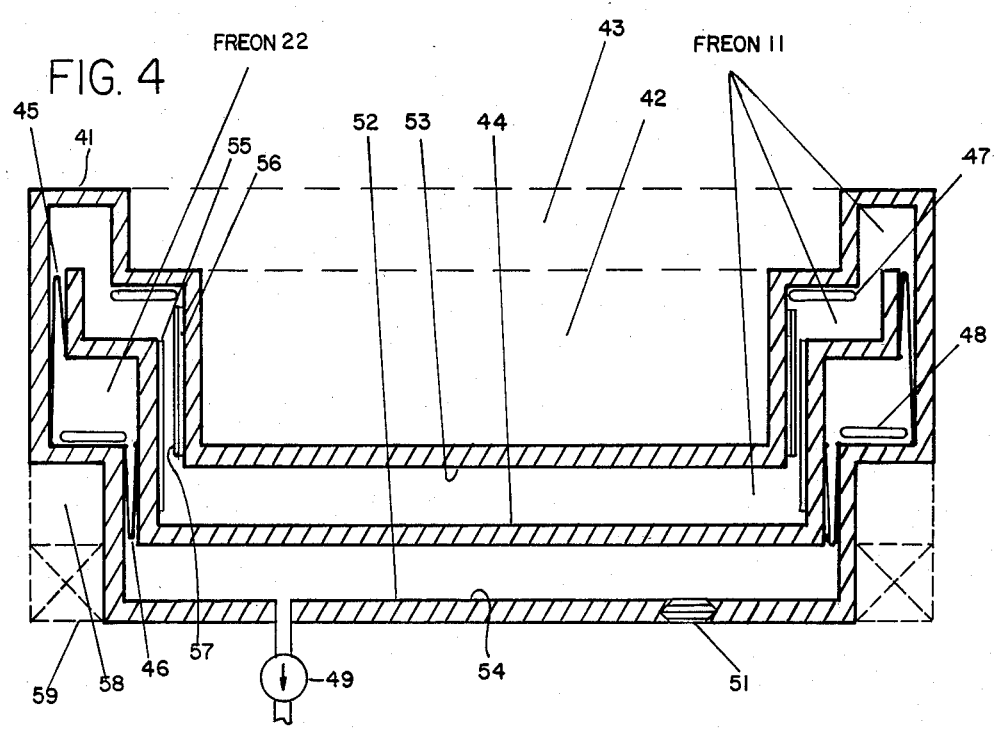
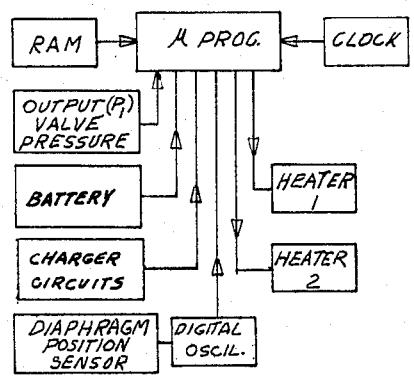
FIG. 5
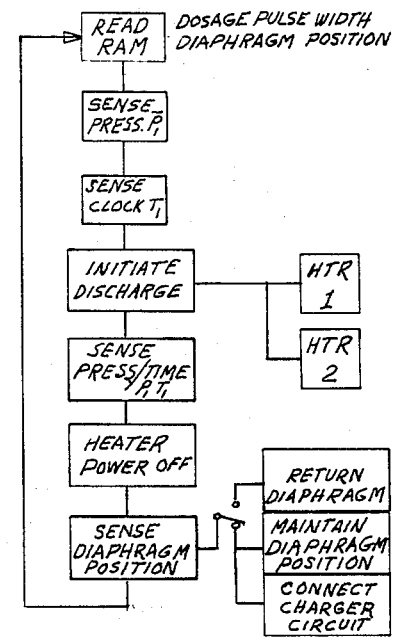
FIG. 6

IMPLANTABLE FLUID DISPENSING SYSTEM

TECHNICAL FIELD

The invention relates to biocompatible containers and implantable electrically controlled systems, for the controlled or programmed dispensing of fluids into a biological system.

In research work using laboratory animals it is sometimes desirable to observe the effects of various serums which are administered to the animal on a temporal basis over relatively long periods of time; e.g., months and years. This could be conveniently done if a precision dispenser can be implanted and controlled either autonomously or from external signals. Also, in the pathology of certain human diseases it is necessary to dispense certain drugs in fluid from on a daily basis over long periods of time, perhaps a lifetime, by syringe, with much discomfort or actual pain to the patient. An implantable fluid drug dispensing system having a long term refillable drug reservoir would relieve some of the trauma associated with this type of medical treatment.

The invention seeks to provide a system for faultless dispensing of fluids in vivo according to a prescribed regimen with the capability of altering the regimen if desired.

BACKGROUND ART

The prior art shows an electronically controllable implantable drug delivery system in which a pump is based on an electro-osmotic principle, since such a motive arrangement could readily be controlled by electronic means, either in response to internal pressure sensors, or by direct actuation by externally induced signals. It will be noted that the prior art does not teach closed loop blood serum sensing; for example blood sugar level, and dispensing of medication to maintain the desired level. The prior art and the present invention are concerned only with faultless medication by dispensing prescribed dosages of drugs, for example, Insulin, according to a prescribed regimen controllable from outside the body in which the drug dispensing unit is implanted, or alternatively, the dispensing of drugs automatically on a monthly basis under the control of long-term timing electronics. The automated system would preferably have an override capability for unscheduled dosage adjustment. For example, diabetic patients often know at the onset of symptoms of hyperglycemia, from long experience with the disease, when, and how much Insulin should be injected. and are capable of operating an implanted Insulin dispensing system manually. The implanted reservoir and electrically operated dispenser saves the diabetic patient the discomfort of periodic, often daily, injections, in favor of refilling the reservoir only once per month, or longer.

The closest prior art described in the literature contemplates the use of an implantable container similar in volume to that of a cardiac pacemaker, having a biocompatible material or coating at the interface with living tissue. The container is divided into three chambers, as shown in FIG. 1, illustrating the prior art. The rightmost chamber 11 is a reservoir which contains the Insulin fluid in quantity sufficient for delivery over an appreciable period; e.g., 1 cc per day for 1 month before replenishment is needed. The exit from this reservoir is connected with an internal conduit 12 of the body, such as an artery, through a tube 13 having a permeable end 13A. Immediately adjacent to this reservoir 11 and separated therefrom by a flexible impermeable diaphragm 14 is a second chamber 15 which contains a drive fluid such as water. This chamber is initially filled without causing deflection of the diaphragm 14 and thus, at rest, does not exert any pressure on the dispensable fluid in the reservoir 11.

When pressure is exerted on the flexible diaphragm 14, Insulin is forced out of the reservoir and into the artery. The pressure is produced by an electro osmotic force. The third chamber 16, to the left of the drive chamber 15, also contains drive fluid (water). The two chambers are separated by a rigid wall 17 which includes a centrally disposed permeable membrane 17A. A source of electrical potential such as a battery, is connected between the two chambers 15, 16. When current is caused to flow, electro-osmotic migration of fluid occurs between the chambers through the membrane 17A. When the current is of one polarity, fluid flows from the leftmost chamber 16 to the center chamber 15, and when the current is of the other polarity, fluid flows in the opposite direction. When flow is toward the flexible diaphragm 14, the compressive force caused thereby reduces the volume of the drug reservoir 11 and Insulin is driven by the resulting pressure into the artery against the internal pressure of the blood flow in the artery. A check valve (not shown) prevents back-flow of blood into the device when the pressure of the blood flow exceeds the pressure in the drug dispensing reservoir.

It might seem that all the drug in the reservoir could be dispensed into the artery as current is applied to transfer the drive fluid from the leftmost chamber 16 to the center chamber 15. However, there is a limitation on that pumping capability of the prior art system. To appreciate this, reference is directed specifically to the ullage space designated as A, above the level of the fluid in the leftmost chamber 16. It is known that in order to pump a fluid from one chamber to another through an interconnecting valve, (e.g., the permeable membrane 17A) the pressure in one chamber must be greater than the pressure in the other. It should be noted that the permeable membrane 17A is directional one way valve dependent on the electrical polarity. Obviously, if the pressures are equal, no flow can take place because the opposing pressures cancel. Thus, if the fluid level in the leftmost chamber 16 is the same as that in the center chamber 15, that is, both are completely filled, and if current is caused to move fluid from the left to the right, as water moves to the right, a vacuum would be formed in the left chamber at A. The resultant pressure differential would produce water back-flow which would continuously return the water to the leftmost chamber. If however, gas fills space A, transfer of water from the left to the right under electro-osmotic impulse could take place, but only up to a limit, which is of practical importance. As water is driven from the left to the right, through the permeable membrane 17A, the space A becomes enlarged. Gas in the space decreases in pressure as a large volume is filled by the confined gas. Thus, when the volume of space A reaches a critical dimension, the pressure differential between the two fluid volumes in chambers 15 and 16 will reach the maximum capability of the pump, and pumping will cease even though current is still being applied. The effect of this is that from the point of view of volume, in order to dispense a given amount of drug, the container would have to be physically much larger than is desirable because the reservoir 11 does not completely empty.

DISCLOSURE OF INVENTION

In accordance with the invention, an electronically controllable drug dispensing unit which makes it possible to dispense more Insulin (for example) for a given reservoir volume, has been devised. In effect, the drive fluid chamber is filled with a liquid-saturated vapor; i.e., the walls of the chamber are wet and the intervening space is filled with saturated vapor; the volume of the gas can be controlled by a controlled heat input so that the difficulty mentioned of requiring a high volume to dispensable drug ratio is drastically lessened. In addition, much finer control of the vapor expansion can be provided by use of an opposing force produced by controlled heating of a similarly saturated vapor. The differential forces can be adjusted so that a balance can be achieved so that no dispensing can take place when that is desired. Furthermore, a total system concept can be applied whereby a reservoir containing the drug and a diaphragm in the reservoir whose movement is under the control of electronic functions occurring at designated times based on a calendared clock chip and microprocessor, automatically perform the medication over a period of one month without intervention by the recipient of the implant. Replenishment of the supply of the drug can take place by means of injecting a syringe needle through the skin and a self-sealing fill valve in the implant. Thus, the recipient need experience the discomfort of an injection only once every thirty days or more, when the drug supply is being replenished in the reservoir.

BRIEF DESCRIPTION OF THE DRAWINGS

The invention will be best understood from the following description taken in conjunction with the accompanying drawings of which:

FIG. 4 is an enlarged cross sectional view of an alternative embodiment of the invention which uses Bellofram rolling seals in lieu of bellows tubes.

FIG. 5 is a block diagram of the electrical control system.

FIG. 6 is a flow diagram of the sequence of steps in the control program executed by the microprocessor.

DESCRIPTION OF THE PREFERRED EMBODIMENTS

Figure 1:
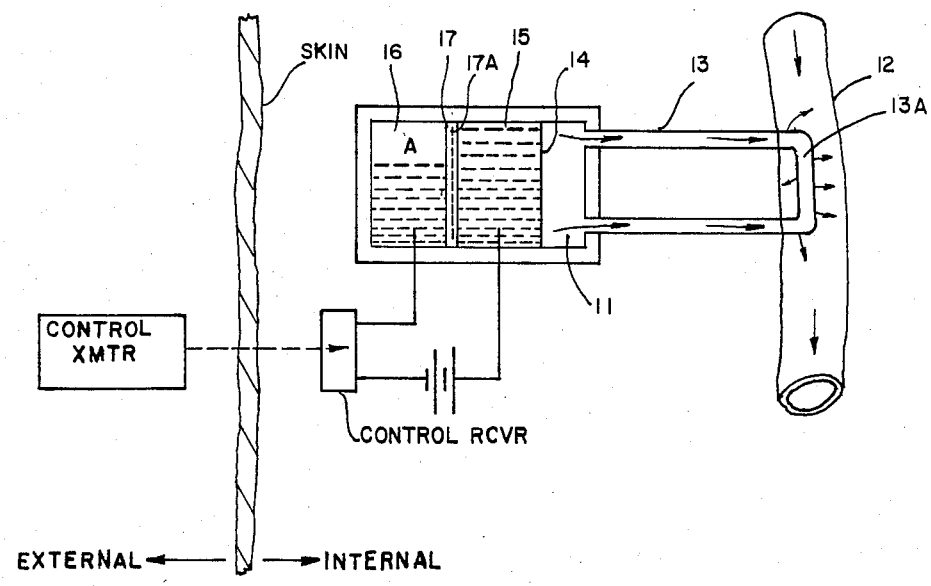
FIG. 1 is a functional schematic of the prior art illustrating the deficiencies thereof.

FIG. 1 has been described in conjunction with the prior art. It shows the general state of the art published by others and includes an external control transmitter which is coupled by electromagnetic signals to an internal receiver. The receiver ostensibly functions to control the application of a polarized voltage to an osmotic pressure driver. Battery charging is also accomplished through electromagnetic coupling to an external power source.

Figures 2, 3:
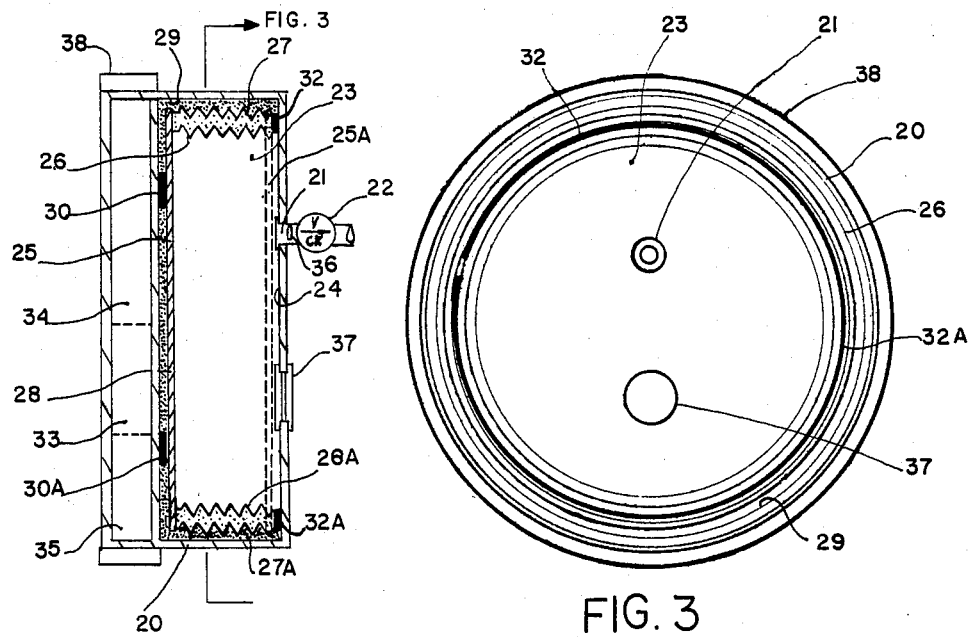
FIG. 2 is a cross sectional view of one possible embodiment of the invention, illustrating two differentially heated Freon cavities in relation to the fluid reservoir cavity.
FIG. 3 is a transverse sectional view through the reservoir and bellows defining the three chambers.

FIG. 2 is a cross sectional view of a drug dispensing device embodying the above-mentioned improvements in the dispensable volume to the unit volume. The device includes an exit port 21 which may communicate through a check valve 22 with a tube connected into an artery for example, or other biological uptake mechanization, or system. The drug containing reservoir 23 is defined by wall 24 and a rigid impermeable diaphragm 25, both of which are connected by a first bellows 26. A second extensible bellows 27 surrounds the first bellows concentrically and is likewise attached to wall 24 and diaphragm 25 to form a second cavity which contains a heat responsive gas such as Freon 22. The interior of the device 20 is closed off by a second rigid impermeable wall 28 which is spaced from diaphragm 25 when the two bellows members are fully extended, to provide a third cavity between diaphragm 25 and wall 28 and between the exterior wall of bellows 27 and the interior surface of wall 29. This third cavity is also filled with a heat sensitive saturated gas such as Freon 11. A positive drive heater 30, 30A is contained within this third cavity and a negative drive heater 32, 32A is contained in the second cavity. Both heaters are connected by wires to the programmed source of electrical power, the program being exercised by a microprocessor located in compartment 33, in combination with a battery in compartment 34 and electronic circuits associated with a memory chip and pressure sensor 36 readout circuits in compartment 35. Pressure sensor 36 monitors the level of pressure at the constant flow valve 22. A high level ($P_1$) from the static state ($P_0$) indicates that a dose of the medication is being administered. The time that $P_1$ is high indicates the size of the dose.

When the device is implanted in a human body, it will reach an equilibrium temperature which is the same as that of the human body. With that temperature, nominally 98.6° F., the Freon 11 vapor pressure in the third cavity, multiplied by the area of the diaphragm 25 which is in contact therewith, would produce a force urging diaphragm 25 toward the wall 24 (see dotted line projection of the diaphragm designated 25A). However, the vapor pressure of the Freon 22 in the second cavity, multiplied by the area of the diaphragm 25 which is in contact therewith, would produce a counter force opposing the force exerted by the Freon 11. This would bring about balancing of the forces and diaphragm 25 would not move.

If heat is supplied by heater 30 to the Freon 11, its vapor pressure will increase tending to drive diaphragm 25 toward the wall 24 causing expulsion of the drug in reservoir 23 through the port 21 (assuming that the Freon 22 is not affected by that heat). If at the same time heat is applied by heater 32 to the Freon 22, depending on the amount of that heat, the rate of movement of the diaphragm 25 toward wall 24 could be regulated or even balanced to hold the diaphragm 25 in a fixed position with respect to wall 24. Thus, when the programmed dispensing has been achieved, the current may be cut off from one or both of the heaters as required to establish a stabilized position of diaphragm 25, at which no further dispensing takes place until a further command is received from the control system. This procedure can be used during replenishment of the drug from an external source. By cutting off current from heater 30, and simultaneously energizing heater 32, diaphragm 25 will move in a direction which will produce a negative pressure in the reservoir 23, thereby drawing in the new supply of the drug. The external supply will normally be a gravity fed IV apparatus or the like. The external supply will be introduced into the reservoir by a syringe needle through self sealing valve 37.

An induction coil 38 provides inductive coupling to an external induction coil connected to an alternating current power source for charging the battery which consists of a group of nickel cadmium cells in compartment 34, through rectifier diodes therein.

FIG. 3 is a transverse section which illustrates the relative position of the reservoir cavity 23, the heater 32, the inside bellows 26 and outside bellows 27 as well as the output port 21 and fill valve 37. Leads to the heaters are fed through wall 28 using ceramic bead feedthroughs from the microprocessor interface circuits. All other construction details are similarly well known state-of-the-art methods and materials. The entire container 20 is preferably coated with collagenated fabric except for the valve orifices, or alternatively, with biocompatible silicone rubber.

FIG. 4 shows an alternative embodiment of the invention wherein a Bellofram rolling seal is used in combination with a shaped diaphragm, in lieu of first and second bellows tubes as used in FIG. 2 embodiments. As shown in FIG. 4, this construction produces even less dead space, particularly when the diaphragm is at its limit position.

The container 41 is shaped to contain a battery chamber 42 and electronics chamber 43 formed into the container externally of the reservoir. A floating diaphragm 44 is mounted on the Bellofram rolling seals 45, 46. The position of these seals provides a chamber for the Freon 22 and the Freon 11 analogous to the second and third chambers respectively of FIG. 2. Heaters 47 and 48 are likewise used to heat the Freon 11 chamber and the Freon 22 chambers respectively, to move the diaphragm 44 in accordance with the dispensing program. The exit valve 49 is a unidirectional, constant flow valve. A fill valve 51 is preferably a puncturable seal valve through which a needle from an external drug supply can be inserted through the skin of the host and the valve so that the reservoir 52 can be refilled. The puncturable seal is of the soft plastic sponge type such as is used in syringe fill bottles, which is self-sealing when the needle is removed.

The Freon 11 chamber areas and the Freon 22 chamber are filled with saturated vapor; i.e., the conditions are such that the walls of the chambers normally are wet with the liquid phase of the specific species of Freon, and the gaseous phase fills the chambers.

The dimensions of diaphragm 44 are such that, at the reservoir FULL position, it is contiguous with wall 53 and when reservoir 52 is empty, it is contiguous with wall 54. A capacitive sensor consisting of insulated rings 55, 56 and insulator 57, monitor the precise position of diaphragm 44 between these two limit positions. The sensing capacitor controls the frequency of a digital oscillator, being proportional to distance from wall 54. If desired, the diaphragm position can be telemetered out to an external recorder by incorporating a transmitter module in the electronics compartment 43 and an antenna located in the charger compartment 58. A charging coil 59 couples the charger circuit to an external power source coil.

FIG. 5 shows the major components of the electrical system. It controls the application of battery power to heaters 1 and 2 (i.e., 47 and 48) for a duration of time to cause valve output pressure $P_1$ to be high from $\bar{P}_1$ and causing fluid to flow from the reservoir through the constant flow valve, thus controling the dosage. The length of time; i.e., the number of pulses counted by the microprocessor circuitry, that the valve pressure $P_1$ is high, assuming a constant flow rate, is set by instructions in the memory RAM. The instructions define the month, day and hour and the prescribed dosage at specified times. With the time and dosage instructions, the microprocessor sets up the differential thermal expansion conditions in the Freon 11 and Freon 22 chambers to cause a pressure pulse at the output of the unidirectional constant flow valve, for the specified time necessary for a dose; e.g., 1 cc to be discharged into the bloodstream of the implant recipient. The diaphragm position, at the end of a dispensing pulse, is recorded in memory as a frequency from the capacitive sensor and associated relaxation oscillator (flip-flop). When the diaphragm 44 FIG. 4 reaches its limit against the wall 54, a return cycle is initiated such that the diaphragm 44 is moved to wall 53.

As shown in the functional flow diagram FIG. 6, the movement of the diaphragm 44 is controlled in response to the dosage pressure pulse width instruction actuating the differential heaters 1, 2. The differential volume is maintained for the last dosage administered by heater differential activation; i.e., the heaters are pulsed for different clock pulse periods. The heater differential is a function of the diaphragm sensor frequency output. Whenever there is no dosage being administered, the charger coil and rectifier circuits are connected to the battery for charging from an external source. If the diaphragm limit is sensed, a return cycle is initiated and a refill warning buzzer is energized. It is deenergized as soon as the diaphragm is moved away from the wall 53, FIG. 4.

A receiver module can be installed in the electronics chamber 43 whereby the microprocessor program is altered to vary the dosage by signals from an external transmitter, if the override capability is desired.

Having described the preferred embodiments, it should be understood that these are exemplary only, and that variations, substitutions, and equivalences that will readily occur to those skilled in the art, are within the scope of the invention and the appended claims.

What is claimed is:

1. A fluid dispensing device for implantation in a biological system, which comprises:
    a container having a closed wall, a closed end, and an end having a first and a second aperture;
    a unidirectional flow valve in said first aperture, adapted to conduct fluid away from said container;
    fill valve means in said second aperture adapted to conduct fluid into said container;
    a reciprocable diaphragm in said container, defining a first volume between the closed end of said container and said diaphragm, and a second volume between said diaphragm and said end having first and second apertures;
    a gas in the first volume of said container;
    a first heater in thermal contact with said gas in the first volume in said container, for expanding said gas;
    an expandable container having first and second concentric, closed, expandable walls and first and second ends, in said container, in contact with said diapragm at the first end, and in contact with the aperture end of said container at the second end, said expandable container surrounding a third volume inward from said first and second concentric expandable walls and between said diaphragm and the aperture end of said container;

a gas in said expandable container; and a second heater in thermal contact with said gas in said expandable container for expanding said gas;

control means connected to said first and second heater adapted to actuate said first and said second heaters autonomously from stored instructions in said control means;

whereby said control means energizes said heaters differentially, urging said diaphragm in one direction or its opposite, forcing fluid out of said unidirectional valve and alternately drawing in fluid through said fill valve means to fill the dispensable fluid third volume in said container.

2. A fluid dispensing device for implantation in a biological system, which comprises:

a container having a closed wall, a closed end, and an end having a first and a second aperture;

a unidirectional flow valve in said first aperture, adapted to conduct fluid away from said container;

fill valve means in said second aperture adapted to conduit fluid into said container;

a reciprocable diaphragm in said container, defining a first volume between the closed end of said container and said diaphragm, and a second volume between said diaphragm and said end having first and second apertures;

a fluorohydrocarbon refrigerant gas in the first volume of said container;

a first heater in thermal contact with said gas in the first volume in said container, for expanding said gas;

an expandable container having first and second concentric, closed, expandable walls and first and second ends, in said container, in contact with said diaphragm at the first end, and in contact with the aperture end of said container at the second end, said expandable container surrounding a third volume inward from said first and second concentric expandable walls and between said diaphragm and the aperture end of said container;

a fluorohydrocarbon refrigerant gas in said expandable container;

a second heater in thermal contact with said gas in said expandable container for expanding said gas;

control means connected to said first and second heater adapted to actuate said first and said second heaters autonomously from stored instructions in said control means;

whereby said control means energizes said heaters differentially, urging said diaphragm in one direction or its opposite, forcing fluid out of said unidirectional valve and alternately drawing fluid through said fill valve means to fill the dispensable fluid third volume in said container.

3. A fluid dispensing device for implantation in a biological system, which comprises:

a container having a closed wall, a closed end, and an end having a first and a second aperture;

a unidirectional flow valve in said first aperture, adapted to conduct fluid away from said container.

fill valve means in said second aperture adapted to conduct fluid into said container;

a reciprocable diaphragm in said container, defining a first volume between the closed end of said container and said diaphragm, and a second volume between said diaphragm and said end having first and second apertures;

a Freon 11 gas in the first volume of said container;

a first heater in thermal contact with said gas in the first volume in said container, for expanding said gas;

an expandable container having first and second concentric, closed, expandable walls and first and second ends, in said container, in contact with said diaphragm at the first end, and in contact with the aperture end of said container at the second end, said expandable container surrounding a third volume inward from said first and second concentric expandable walls and between said diaphragm and the aperture end of said container;

a Freon 22 gas in said expandable container;

a second heater in thermal contact with said gas in said expandable container for expanding said gas;

control means connected to said first and second heater adapted to actuate said first and second heaters autonomously from stored instructions in said control means;

whereby said control means energizes said heaters differentially, urging said diaphragm in one direction or its opposite, forcing fluid out of said unidirectional valve and alternately drawing fluid through said fill valve means to fill the dispensable fluid third volume in said container.

4. A fluid dispensing device for implantation in a biological system, which comprises:

a container having a closed wall, a closed end, and an end having a first and a second aperture;

a unidirectional flow valve in said first aperture, adapted to conduct fluid away from said container;

fill valve means in said second aperture adapted to conduct fluid into said container;

a reciprocable diaphragm in said container, defining a first volume between the closed end of said container and said diaphragm, and a second volume between said diaphragm and said end having first and second apertures;

a saturated vapor gas in the first volume of said container;

a first heater in thermal contact with said gas in the first volume in said container, for expanding said gas;

a first bellows having a first end connected to said diaphragm in fluid-tight relationship thereto and a second end connected in a fluid-tight relationship to the aperture end of said container;

a second bellows concentric with said first bellows, spaced radially therefrom, having a first end connected to said diaphragm in fluid-tight relationship thereto, and a second end connected in fluid-tight relationship to the aperture end of said container, creating a volume between bellows;

a saturated vapor in the volume created by said first and said second bellows, said diaphragm, and said aperture end of said container; and, a second heater in contact with said saturated vapor;

control means connected to said first and second heater, adapted to actuate said first and said second heaters autonomously from stored instructions in said control means;

whereby said control means energizes said heaters differentially urging said diaphragm in one direction or its opposite, forcing fluid out of said unidirectional valve and alternately drawing in fluid through said fill valve means to fill the dispensable fluid third volume in said container.

5. A fluid dispensing device for implantation in a biological system, which comprises:
- a container having a closed wall, a closed end, and an end having a first and a second aperture;
- a unidirectional flow valve in said first aperture, adapted to conduct fluid away from said container;
- fill valve means in said second aperture adapted to conduct fluid into said container;
- a reciprocable diaphragm in said container, defining a first volume between the closed end of said container and said diaphragm, and a second volume between said diaphragm and said end having first and second apertures;
- a saturated vapor gas in the first volume of said container;
- a first heater in thermal contact with said gas in the first volume in said container, for expanding said gas;
- a first bellows having a first end connected to said diaphragm in fluid-tight relationship thereto and a second end connected in a fluid-tight relationship to the aperture end of said container;
- a second bellows concentric with said first bellows, spaced radially therefrom, having a first end connected to said diaphragm in fluid-tight relationship thereto, and a second end connected in fluid-tight relationship to the aperture end of said container, creating a volume between bellows;
- a saturated vapor in the volume created by said first and said second bellows, said diaphragm, and said aperture end of said container;
- a second heater in contact with said saturated vapor;
- a calendar clock providing year, month, day and seconds timing pulses;
- a memory having stored data indicating the number of seconds clock pulses the unidirectional valve pressure $P_1$ should be high, and the day of the month and time of the day the unidirectional valve pressure $P_1$ should be high, the last position of said diaphragm after a $P_1$ event, and procedural instructions for a microprocessor;
- a valve pressure sensor adapted to read the pressure $P_1$ at said unidirectional flow valve input;
- a diaphragm position sensor;
- a microprocessor programmed to read said memory, said diaphragm position sensor, and said pressure sensor, and actuate said first and second heaters to move said diaphragm in accordance with procedural instructions and data in said memory; and
- an interface means adapted to set up circuits for executing control functions from signals from said microprocessor;
- whereby a time pules energizes said first and second heaters differentially causing movement of said diaphragm in the direction of the greater gas expansion force and no movement when there is no differential, and sensing the positing of the diaphragm after each movement for logging the dosage and initiating refill cycle, is done automatically.

* * * * *